United States Patent [19]
Clapper et al.

[11] Patent Number: 5,512,474
[45] Date of Patent: Apr. 30, 1996

[54] CELL CULTURE SUPPORT CONTAINING A CELL ADHESION FACTOR AND A POSITIVELY-CHARGED MOLECULE

[75] Inventors: David L. Clapper, Shorewood; Wei-Shou Hu, Falcon Heights, both of Minn.

[73] Assignee: BSI Corporation, Eden Prairie, Minn.

[21] Appl. No.: 208,916

[22] Filed: Mar. 9, 1994

Related U.S. Application Data

[63] Continuation of Ser. No. 891,509, May 29, 1992, abandoned.

[51] Int. Cl.$^6$ .............................. C12N 5/00; C12N 11/08; C12M 3/00
[52] U.S. Cl. .................................. 435/240.243; 435/180; 435/240.1; 435/240.23; 435/240.24; 435/299.1; 435/289.1; 435/305.1; 530/810; 530/815
[58] Field of Search .................................... 435/174, 176, 435/177, 178, 180, 240.1, 240.23, 240.24, 240.243, 284; 530/810, 815

[56] References Cited

U.S. PATENT DOCUMENTS

| | | | |
|---|---|---|---|
| 4,036,693 | 7/1977 | Levine et al. | 495/1.8 |
| 4,293,654 | 10/1981 | Levine et al. | 435/241 |
| 5,114,855 | 5/1992 | Hu et al. | 435/174 X |

FOREIGN PATENT DOCUMENTS

WO9107485  5/1991  WIPO.

OTHER PUBLICATIONS van Wezel, A. L., "Growth of Cell–Strains and Primary Cells on Micro–Carriers in Homogenous Culture", *Nature* 216:64–65 (1967).
Grinnell, F., "Cellular Adhesiveness and Extracellular Substrata", *Internat. Rev. Cytology* 53:65–144 (1978).
*Microcarrier Cell Culture. Principles and Methods*, Pharmacia Fine Chemicals, Uppsala, Sweden, pp. 5–33 (1981).
Kleinman, H. K., Luckenbill–Edds, F. W. Cannon, and G. C. Sephel, "Use of Extracellular Matrix Components for Cell Culture", *Anal. Biochem.* 166:1–13 (1987).
Lai, C–S, E. G. Ankel and L. E. Hopwood, "Membrane Fluidity of Chinese Hamster Ovary Cells on Plasma Fibronectin–Coated Microcarriers", *Exp. Cell Res.* 150:77–83 (1984).
Himes, V. B. and W. S. Hu, "Attachment and Growth of Mammalian Cells on Microcarriers with Different Ion Exchange Capacities", *Biotech. Bioeng.* 29:1155–1163 (1987).
Kim, J–H, H–S Lim, B–K Han, M. V. Peshwa, and W. S. Hu, "Characterization of Cell Growth and Improvement of Attachment Kinetics on Macroporous Microcarriers", presented at the Fourth Annual Meeting of the Japanese Association for Animal Cell Technology, Fukuoka, Japan (Nov. 1991).
Butler, M., "Growth Limitations in Microcarrier Cultures", *Adv. Biochem. Eng./Biotech.* 34:57–84 (1987).
Yamada, K. M., "Cell Surface Interactions with Extracellular Materials,", *Ann. Rev. Biochem.* 52:761–799 (1983).
Ruoslahti, E. and M. Pierschbacher, "Arg–Gly–Asp: A versatile Cell Recognition Signal," *Cell* 44:517–518 (1986).
Pierschbacher, M. D. and E. Ruoslahti, "Cell Attachment Activity of Fibronectin can be Duplicated by Small Synthetic Fragments of the Molecule," *Nature* 309:30–33 (1984).
Graf, J. et al., "Identification of an Amino Acid Sequence in Laminin Mediating Cell Attachment, Chemotaxis, and Receptor Binding," *Cell* 48:989–996 (1987).
Levine, et al, *Biotechnol. Bioeng.* vol. 21, 821 (1979).
Buck, C. A. and A. F. Horwitz, "Cell Surface Receptors for Extracellular Matrix Molecules," *Ann. Rev. Cell Biol.* 3:179–205 (1987).

*Primary Examiner*—David M. Naff
*Attorney, Agent, or Firm*—Philip M. Goldman; James R. Haller; Gregory P. Kaihoi

[57] ABSTRACT

A combination of a cell adhesion factor and a positively-charged molecule are bound to the surface of a cell culture support of a bioreactor to improve cell attachment and stabilize cell growth. The positively charged molecule is preferably polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor is preferably fibronectin, laminin, collagen, vitronectin or tenascin, or fragments or analogs having a cell binding domain thereof. The positively-charged molecule and the cell adhesion factor can be covalently bound to the supporting surface. In another embodiment, the positively-charged molecule and the cell adhesion factor are covalently bound to one another and either the positively-charged molecule or the cell adhesion factor is covalently bound to the supporting surface. Also, the positively-charged molecule or the cell adhesion factor or both cam be provided in the form of a stable coating non-covalently bound around the surface of the support. The cell culture support may be in the form of a microcarrier and can be made of polystyrene or polypropylene

12 Claims, No Drawings

CELL CULTURE SUPPORT CONTAINING A CELL ADHESION FACTOR AND A POSITIVELY-CHARGED MOLECULE

This invention was made in part with government support under grant number ISI- 8760680 (National Science Foundation). The government has certain rights in the invention.

This application is a continuation of application Ser. No. 07/891,509, filed May 29, 1992, now abandoned.

FIELD OF THE INVENTION

This invention relates to cell culture surfaces of bioreactors in the field of cell biology and particularly to methods of improving the surfaces to obtain better cell attachment and cell growth.

BACKGROUND OF THE INVENTION

Cell culture of mammalian cells has long been used for the production of many vaccines and genetically engineered proteins. Animal cells are generally categorized according to their anchorage-dependence. Some cell types, such as lymphocytes, can grow in suspension; others, called "anchorage-dependent", including fibroblasts and epithelial and endothelial cells, must attach to a surface and spread out in order to grow. Other cells can grow either in suspension or anchored to a surface.

Anchorage-dependent cells have historically been cultivated on the walls of roller bottles or non-agitated vessels such as tissue culture flasks, which are used in many laboratories. As the necessity has developed to provide large amounts of certain antiviral vaccines, genetically engineered proteins, and other cell-derived products, attempts have been made to develop new systems for larger scale production of cells.

The first focus of this development effort was to increase the growth surface area per unit vessel volume and to implement convenient and appropriate environmental controls. Some of these technologies involved the use of packed-glass beads, stacked plates, rotating multiple tubes, and roller bottles with spiral films inside.

Among the most important advances in the field of cell culture technology have been the use of microcarriers and more recently, the use of hollow fiber systems. Original microcarriers developed by van Wezel (van Wezel, A. L., "Growth of Cell-Strains and Primary Cells on Micro-carders in Homogeneous Culture," *Nature* 216:64–65 (1967)) consisted of positively charged DEAE-dextran beads suspended in culture media in a stirred vessel. Cells would attach to the bead surface and grow as a monolayer.

Hollow fiber bioreactor configurations serve to compartmentalize the bioreactors. In one common configuration, these units allow cells to grow on the outside surfaces of bundles of parallel fibers enclosed in an outer compartment. Nutrient- and gas-enriched medium flows through the fibers' hollow centers. Cell products are concentrated in the outer compartment of the bioreactor because the inner surface of the fiber includes an ultrafiltration membrane that excludes large molecular-weight cell products.

Bioreactors have certain minimum requirements: an aeration system is required to bring the correct amount of oxygen to the cells without causing shear damage; surfaces are required for supporting anchorage-dependent cells; and means are required to enable operators to sample and monitor the contents of the bioreactor without contaminating the culture.

The various bioreactors have encountered similar problems in culturing cells. With respect to anchorage-dependent cells, specific cell culture parameters in need of improvement include: (1) better initial attachment and growth of cells to decrease the concentration of cells required for inoculation of a culture; (2) improved long-term cell adhesion, viability, and productivity to increase the useful life of the bioreactor; and (3) alteration of growth conditions to allow lower concentrations of serum to be used in the culture medium.

The adhesion of cells to a surface is a multi-step process, consisting of initial attachment (characterized by weak binding and little cell shape change) followed by cell spreading (which produces stronger binding of cells to the substrate) (Grinnell, F., "Cellular Adhesiveness and Extracellular Substrata", *Internat. Rev. Cytology* 53:65–144 (1978)). The initial attachment can be mediated by non-specific mechanisms such as charged surfaces (Grinnell, F., "Cellular Adhesiveness and Extracellular Substrata", *Internat. Rev. Cytology* 53:65–144 (1978) and *Microcarrier Cell Culture. Principles and Methods,* Pharmacia Fine Chemicals, Uppsala, Sweden, pages 5–33 (1981)). In contrast to initial attachment, cell spreading seems to require the presence of specific receptor-ligand interactions between cell surface receptors and certain cell adhesion glycoproteins, such as fibronectin, laminin, and collagens (Kleinman, H. K., Luckenbill-Edds, F. W. Cannon, and G. C. Sephel, "Use of Extracellular Matrix Components for Cell Culture", *Anal. Biochem.* 166:1–13 (1987)). All three types of these glycoproteins have been purified and added to tissue culture surfaces to promote cell adhesion and cell growth (Kleinman, H. K., Luckenbill-Edds, F. W. Cannon, and G. C. Sephel, "Use of Extracellular Matrix Components for Cell Culture", *Anal. Biochem.* 166:1–13 (1987)). Studies have shown that a coating of gelatin or denatured collagen on microcarders facilitates the attachment and growth of mammalian cells (*Microcarrier Cell Culture. Principles and Methods,* Pharmacia Fine Chemicals, Uppsala, Sweden, pages 5–33 (1981)).

Early microcarriers were in the form of DEAE-derivatized dextran beads. The use of these beads, however, produced certain deleterious effects. For example, a high initial cell death rate and inadequate cell growth was observed with cells attached to beads that contain an ion-exchange capacity that was too high. Two methods that have been proposed to overcome some of these deleterious effects involved (1) attaching a lower density of positively-charged molecules to the beads, in order to provide a charge capacity of 0.1–4.5 meg/g dextran (see, e.g., U.S. Pat. No. 4,293, 654), and (2) adsorbing polyanions onto the positively-charged microcarriers, in order to neutralize some of the excess charge (see, e.g., U.S. Pat. No. 4,036,693).

It has been reported that the adsorption of an attachment glycoprotein (fibronectin) from serum onto the surface of positively-charged microcarriers promotes cell spreading in non-agitated cultures (Lai, C-S, E. G. Ankel and L. E. Hopwood, "Membrane Fluidity of Chinese Hamster Ovary Cells on Plasma Fibronectin-Coated Microcarriers", *Exp. Cell Res.* 150:77–83 (1984); *Microcarder Cell Culture. Principles and Methods,* Pharmacia Fine Chemicals, Uppsala, Sweden, pages 5–33 (1981)). On the other hand, the presence of adsorbed fibronectin has been shown to have the undesirable effect of decreasing the rate of cell attachment to stirred, i.e., agitated, microcarders (Himes, V. B. and W. S. Hu, "Attachment and Growth of Mammalian Cells on Microcarders with Different Ion Exchange Capacities", *Biotech. Bioeng.* 29:1155–1163 (1987)).

Cell adhesion proteins (e.g., fibronectin, laminin, and collagens) used in the absence of positively-charged groups have worked well to promote the growth and spreading of cells in non-agitated cell culture devices, but do not appear to effectively attract and attach cells with a sufficient rate or tenacity in agitated devices.

The incorporation of positive charges onto macroporous gelatin microcarriers was reported to greatly improve the rate of cell attachment to these microcarriers (Kim, J-H, H-S Lim, B-K Han, M. V. Peshwa, and W. S. Hu, "Characterization of Cell Growth and Improvement of Attachment Kinetics on Macroporous Microcarriers", presented at the Fourth Annual Meeting of the Japanese Association for Animal Cell Technology, Fukuoka, Japan (November 1991)).

Most currently used microcarriers use porous non-rigid dextran as a support matrix. This compressible matrix is believed by some to reduce the potential for damage to the microcarriers and attached cells when the microcarriers collide in agitated reactors *Microcarder Cell Culture. Principles and Methods*, Pharmacia Fine Chemicals, Uppsala, Sweden, pages 5–33 (1981)). Such porous microcarriers, however, frequently also have the disadvantage of retaining cellular products that are secreted into the medium (thus complicating the harvesting of desired cell products) as well as the disadvantage of adsorbing growth factors and other serum components, thus reducing their levels in the culture media (Butler, M., "Growth Limitations in Microcarder Cultures", *Adv. Biochem. Eng./Biotech.* 4:57–84 (1987)).

Polystyrene microcarriers produce superior cell growth, with higher recovery of products; however, currently available polystyrene microcarders produce unacceptably low rates of cell attachment.

While not considered to be art against the instant application, PCT application publication No. WO 91/07485, published May 30, 1991 (now abandoned), which corresponded to U.S. Ser. No. 434,092 (assigned to the assignee of the instant application) describes, inter alia, a bioreactor cell culture surface having a cell adhesion factor and positively charged chemical moiety.

In spite of the art and other earlier efforts described above, those involved in the cell culture of anchorage-dependent cells remain desirous of a bioreactor support surface having both cell adhesion factor and positive charge provided in a manner that is stable in the course of agitation during incubation.

SUMMARY OF INVENTION

The present invention provides a cell culture system comprising a support material providing a surface for the attachment of cells, the surface beating an effective and stable combination of positively-charged molecule and cell adhesion factor.

In one embodiment, the stable combination involves cell adhesion factor and positively-charged molecule, each being separately covalently bound to the supporting surface. Desirably, one or both of the cell adhesion factor and the positively-charged molecule is covalently linked to the surface through a linking group, the linking group including the residue of a latent reactive group employed to covalently bond to the supporting surface.

In another embodiment, the cell adhesion factor and the positively-charged molecule of the composition can each be covalently bound to one another, and either the cell adhesion factor or the positively-charged molecule bound to the supporting surface, desirably through a linking group as described above.

Yet another, and a preferred, embodiment, involves the use of a stable coating around or on the surface of the support material, such as a shell around a bead. The coating can comprise either the adhesion factor or the charged molecule, or both. In the event the coating comprises the adhesion factor alone, for instance, the charged molecule can be bound to the cell adhesion factor coating. In the alternative, the coating can comprise the charged molecule, in which case the adhesion factor can be bound thereto. In yet another embodiment, the coating can include, or itself be provided by, one or more other materials, that may not be considered either positively charged molecules or a cell adhesion factors, as defined herein, to which can be bound the charged molecule and/or cell adhesion factor. In each of the foregoing embodiments, the resultant shell serves to stably retain the combination of charged molecule and adhesion factor in position on or around the support surface, without the covalent binding of either directly to the support surface.

Preferably, both the cell adhesion factor and positively-charged molecule are uniformly and homogeneously distributed on the surface. In a preferred embodiment, the two form a homogeneous blend on the surface, and are located with respect to each other on the surface in such a manner that both are presented, i.e., physically accessible, to cells to be affixed to the surface. The supporting surface of the cell culture system, e.g., the cell-contacting surface of a bioreactor of the present invention, bears a density of a cell adhesion factor and a density of positively-charged molecule that are sufficient to promote and stabilize cell attachment to the surface.

The present invention further provides a method of attracting and growing anchorage-dependent cells on a supporting surface of a cell culture system, comprising the steps of: (a) providing a support material comprising a supporting surface bearing an effective and stable combination of positively-charged molecule and cell adhesion factor, and (b) combining anchorage-dependent cells with the supporting surface in an aqueous environment under conditions in which the cells are attracted to and grow on the supporting surface.

DETAILED DESCRIPTION OF THE INVENTION

The present invention provides a cell culture system comprising a support material providing a surface for the attachment of cells, the surface bearing an effective and stable combination of positively-charged molecule, which will alternatively be referred to herein as the "charged molecule", and cell adhesion factor.

As described more fully below, the positively-charged molecule is a preferably a polymer and is preferably "enzymatically resistant", in that it is not readily degraded by the types of enzymes typically present in cell culture fluids, nor is it degraded in the course of its use to an extent where it no longer serves its desired purpose. The polymer is preferably also "synthetic", in that it is not naturally occurring.

The word "effective", as used herein, refers to the ability of the charged molecule and adhesion factor, in combination, to attract anchorage-dependent cells to the surface of the cell culture system, in order to allow the growth and/or spreading of such cells once attracted.

The term "stable combination", as used herein, refers to the presence of both charged molecule and adhesion factor in a form suitable for their intended purpose, e.g., for the attachment, spreading, and growth of anchorage-dependent cells to the surface in the course of agitated incubation.

The charged molecule and adhesion factor are attached to the support surface, e.g., covalently and/or by the formation of a shell such as described above, in a manner sufficient for their intended use. Frequently, such use includes the use of agitation, for example, the agitation of a cell culture plate or bottle in the course of its incubation. Preferred systems provide the claimed combination in a form having sufficient stability to be useful in the course of such agitation.

A number of cell culture systems, which will be alternatively referred herein to as bioreactors, exist for culturing anchorage-dependent cells, and the invention is not dependent upon any particular type or configuration of bioreactor. The "supporting surface" of this invention, i.e., the surface of a bioreactor that is intended to physically contact and support growing cells, bears an effective and stable combination of positively-charged molecule and cell adhesion factor.

Bioreactors of the present invention can be prepared having a support material providing a surface for the attachment of cells. A wide variety of compounds can be employed as the support material, the primary considerations being that they are preferably neither soluble or swellable in water. Suitable support materials provide a surface that exhibits an optimal combination of such properties as rigidity, surface area, ease of preparation and use, and cost. Preferred support materials are rigid, i.e., do not swell or expand appreciably in an aqueous environment. Preferred support materials, for instance, expand less that about fifty percent, and preferably less than about twenty percent, in any dimension when placed from the dry state into isotonic saline.

Preferred support materials are synthetic polymers, including oligomers, homopolymers, and copolymers resulting from either addition or condensation type polymerizations. Examples of suitable addition type polymers include, but are not limited to, acrylics such as those polymerized from methyl acrylate, methyl methacrylate, acrylic acid, methacrylic acid, acrylamide, and methacrylamide; vinyls such as styrene, vinyl chloride, vinyl pyrrolidone, and vinyl acetate; polymers formed of ethylene, propylene, and tetrafluoroethylene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, and poly(ethylene terephthalate).

Other suitable support materials include ceramics, e.g., silicon nitride, silicon carbide, zirconia, and alumina, as well as glass, silica, and the like.

Bioreactors can be provided in any suitable form, for instance, as membranes, tubes, microtiter wells, columns, hollow fibers, roller bottles, plates, dishes, and solid, hollow, or porous beads. For bioreactors in the form of microcarriers, such as beads, the size of the microcarrier bead used will depend upon the cell type being cultivated. Larger beads minimize the required concentration of cells needed to inoculate a culture and maximize the growth rate, whereas small beads maximize the surface area and require less vigorous mixing to remain in suspension. Also, different cell types grow optimally on different sizes of microcarriers.

The system of the present invention improves the attachment and growth of "anchorage-dependent cells", i.e., cells that generally need to attach to a support surface and spread out in order to grow. Grinnell, F., "Cellular Adhesiveness and Extracellular Substrata," *International Rev. Cytology* 53:65–114 (1978). Anchorage-dependent cells useful in the system of the present invention, include, but are not limited to, green monkey kidney (Vero) cells, Chinese hamster ovary (CHO) cells and normal rat kidney fibroblast cells (e.g., NRK- 49F). Cell attachment to bioreactor surfaces, as described in the present invention, can either be receptor-mediated, i.e., by the use of cell attachment factors, and/or can be charge-based. With receptor-mediated cell attachment, receptors on the cell surface recognize and bind to cell adhesion factors carried by the bioreactor surfaces. Yamada, K. M., "Cell Surface Interactions with Extracellular Materials," *Ann. Rev. Biochem.* 52:761–799 (1983). Kleinman, H. K., L. Luckenbill-Edds, F. W. Cannon, and G. C. Sephel, "Use of Extracellular Matrix Components for Cell Culture," *Anal. Biochem.* 166:1–13 (1987). Cell adhesion factors immobilized onto bioreactor surfaces are believed to promote receptor-mediated cell attachment.

In the alternative, positively-charged molecules employed on bioreactor surfaces of the invention can promote cell attachment to the surface by promoting ionic binding between the positively-charged molecules and cell constituents, such as negatively-charged glycoproteins and phospholipids carried on cell surfaces. By combining the use of cell adhesion factors and positively-charged moieties on the same bioreactor surface, the present invention provides the opportunity for either or both types of cell attachment, likely by a mechanism involving both receptor-mediated and non-receptor- mediated (i.e., charge-related) cell attachment.

"Cell adhesion factor", as used herein, refers to a molecule that mediates the adherence of cells, via the cell's receptors, to a support surface, e.g., in order to increase the rate at which such cells grow and spread on that surface. Suitable cell adhesion factors include cell adhesion proteins, cell adhesion protein peptide fragments, and synthetic peptide analogs. Examples of preferred cell adhesion factors useful with this invention include such cell adhesion proteins as laminin, fibronectin, collagens (all types), vitronectin, and tenascin; cell adhesion peptides such as the cell attachment domain of fibronectin identified as the tripeptide (RGD) and the cell attachment domain of laminin identified as the pentapeptide (YIGSR) of laminin; as well as other binding domains of these and other cell adhesion proteins and functional synthetic analogs thereof.

Cell adhesion proteins typically have one or more domains that mediate binding to cell surface receptors. These cell attachment domains consist of specific amino acid sequences that can be chemically synthesized to produce cell adhesion peptides that possess the cell attachment properties of the intact cell adhesion proteins. Two examples of such cell adhesion peptides are the tripeptide (RGD or arg-gly-asp) sequence present in fibronectin and the pentapeptide (YIGSR or tyr-ile-gly-ser-arg) sequence present in laminin: Ruoslahti, E. and M. Pierschbacher, "Arg-Gly-Asp: A versatile Cell Recognition Signal," *Cell* 44:517–518 (1986); Pierschbacher, M. D. and E. Ruoslahti, "Cell Attachment Activity of Fibronectin can be Duplicated by Small Synthetic Fragments of the Molecule," *Nature* 309:30–33 (1984). Graf, J. et al., "Identification of an Amino Acid Sequence in Laminin Mediating Cell Attachment, Chemotaxis, and Receptor Binding," *Cell* 48:989–996 (1987).

Cell adhesion proteins are primarily those that are naturally occurring and quite large, with molecular weights above about 100,000 daltons. Cell adhesion peptides generally are short amino acid sequences derived from or functionally analogous to the binding domains of the cell adhesion proteins. Desirably, cell adhesion peptides used in this invention have between about 3 and about 30 amino acid residues in their amino acid sequences. Preferably, cell adhesion peptides have not more than about 15 amino acid residues in their amino acid sequences.

Cell adhesion factor and positively-charged molecule are used at a surface density sufficient to promote initial cell attachment and to stabilize attachment of the cells to the surface. The density of each will vary and will depend in part upon such factors as the configuration of the bioreactor, the material with which the supporting surface is made, and the cells to be attached to the surface.

A sufficient density of cell adhesion factor should be carded by the bioreactor's supporting surface to promote cell attachment and growth. For example, the density of cell adhesion factor will desirably range from about 0.01 to about 1000 picomoles of factor per square centimeter of support surface. With cell adhesion proteins, the desirable range is from about 0.01 picomoles to about 100 picomoles, and with cell adhesion peptides, the desirable range is from about 0.1 picomole to about 1000 picomoles per square centimeter of support surface.

"Positively-charged molecule", which will be used interchangeably with its preferred embodiment, "positively-charged polymer", refers herein to a molecule that increases the positive charge density of the support surface. Suitable charged molecules provide an optimal combination of such properties as solubility, charge density, film-forming ability, and hydrophilicity. Examples of suitable molecules are polymers that possess positively charged groups together with other functionalities that enable the polymer to be stably coated (e.g., covalently) onto the support surface. Examples of charged groups useful in such polymers are primary, secondary, and tertiary amines as well as quaternary ammonium salts. Such charged groups can be incorporated into a polymer in the form of monomers such as N-(3-aminopropyl)methacrylamide (APMA), N-(3-dimethylaminopropyl)methacrylamide, methacrylamidopropyl trimethylammonium chloride, aminostyrene, vinyl pyridine, ornithine, and lysine. Other groups suitable for the incorporation of positive charge into a molecule include amidines, guanidines, hydrazines, and phosphonium salts.

Preferred charged polymers are both synthetic and enzymatically resistant. "Synthetic", as used herein, means either polymerized from monomers and/or oligomers, at least some of which include the positively charge group or groups of choice, and/or prepared by the chemical modification of naturally-occuring polymeric backbones. The synthetic polymers can be prepared by the use of addition- or condensation-type polymerization mechanisms. Addition-type polymers include, but are not limited to, acrylics such as those polymerized from methyl acrylate, methyl methacrylate, hydroxyethyl acrylate, hydroxyethyl methacrylate, acrylic acid, methacrylic acid, acrylamide, and methacrylamide, as well as vinyls such as styrene, vinyl chloride, vinyl pyrrolidone, vinyl acetate, ethylene, propylene, and tetrafluoroethylene. Examples of condensation type polymers include, but are not limited to, nylons such as polycaprolactam, polylauryl lactam, polyhexamethylene adipamide, and polyhexamethylene dodecanediamide, as well as polyurethanes, polycarbonates, and polyimides.

Examples of other synthetic polymers within the scope of the present invention include derivatives of cellulose, including, but not limited to, diethyl aminoethyl cellulose, carboxy methyl cellulose, aminoethyl cellulose, and chitosan, which is a synthetic product of the naturally occurring compound chitin.

"Enzymatically resistant", as used herein, means not readily degradable by the enzymes typically present in cell culture fluid, e.g., proteases, glycosidases (such as lysozyme), and the like. Such synthetic polymers preferably also incorporate one or more reactive functionalities, in order to enable the attachment of the polymer to support surfaces of the present invention. Such reactive functionalities can be provided by the same moieties that provide the positive charge (e.g., amine groups), or can be separately provided, for example, by the presence of carboxyl, hydroxyl, or sulfhydryl groups or the incorporation of latent reactive groups as described above.

The positively-charged molecule is used at a density sufficient to promote initial cell attachment and to stabilize attachment of the cells to the surface. The appropriate density can be determined by those skilled in the art, based on the present specification, and will depend upon such factors as the configuration of bioreactor used, the material from which the supporting surface is made, and the cells that are to be attached to the surface. A sufficient density of positively-charged molecule should be carded by the bioreactor's supporting surface to provide the surface with an ion-exchange capacity at a physiologic pH to promote initial cell attachment. Ion-exchange capacity is a quantitative measurement of the amount of a negatively-charged reagent that can bind to the bioreactor surface, per unit area. The rate of cell attachment to a bioreactor surface is reported to correlate more closely with ion-exchange capacity than with charge density: Himes, V. B. and W. S. Hu, "Attachment and Growth of Mammalian cells on Microcarders with Different Ion Exchange Capacities," *Biotechnol. Bioeng.* 29:1155–1163 (1987). Desirably, the density of positively-charged molecule in this invention is such as to provide the bioreactor surface with an ion-exchange capacity in the range of about 1 to about 100 microequilavents per square centimeter of support surface.

The exchange capacity of a DEAE-dextran bead microcarder can be determined by titration of bound DEAE-HCl molecules as described by Levine, et at, *Biotechnol. Bioeng.* Vol. 21,821 (1979), the disclosure of which is incorporated herein by reference. The DEAE-dextran microcarriers are typically washed with 0.1 molar HCl (0.5 L/g dry dextran beads) to allow for the saturation of the exchange sites with chloride ions. In order to remove unbound chloride ions, the beads are rinsed with dilute HCl ($10^{-4}$ M, 0.8 L/g dry dextran beads). The beads are then washed with 10% (w/w) sodium sulfate (75 mL/g dry dextran beads) and the filtrate collected. The last wash displaces the bound chloride ions with sulfate ions. 100 ml of the filtrate is titrated with 1.0 molar silver nitrate in the presence of potassium chromate as an indicator (1 mL 5 % w/w solution).

Different types of cell adhesion factors, such as gelatin and one or more cell attachment peptides, can be carried upon the same supporting surface. Cell adhesion factors promote cell attachment by binding to specific receptors on the cell surface, and some cell types have receptors for more than one type of cell adhesion factor; Buck, C. A. and A. F. Horwitz, "Cell Surface Receptors for Extracellular Matrix Molecules," *Ann. Rev. Cell Biol.* 3:179–205 (1987). Immobilizing different types of cell adhesion factors upon the same supporting surface can allow the binding of more receptors on each cell than would occur with a simple type of immobilized cell adhesion factor, thereby resulting in faster and more tenacious cell attachment to the supporting surface.

Preferably, cell adhesion factors and positively-charged molecules are each covalently bound to the supporting surface. Desirably, one or both of the cell adhesion factor and the positively-charged molecule is covalently linked to the surface through a linking group, the linking group including the residue of a latent reactive group through which the cell adhesion factor or positively-charged molecule is covalently bonded to the supporting surface. We have discovered that covalent bonding to the supporting surface of a cell adhesion factor that has attached to it a positively-charged molecule leads to faster cell attachment than occurs to supporting surfaces that have attached only a cell adhesion factor or a positively-charged molecule.

Latent reactive groups, broadly defined, are groups which respond to specific applied external stimuli to undergo active species generation with resultant covalent bonding to an adjacent support surface. Latent reactive groups are those groups of atoms in a molecule which retain their covalent bond unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups may be chosen to be responsive to various portions of the electromagnetic spectrum, and latent reactive groups that are responsive to ultraviolet, visible or infrared portions of the spectrum are preferred. Latent reactive groups as described are generally well known.

The azides constitute a preferred class of latent reactive groups and include arylazides ($C_6R_5N_3$) such as phenyl azide and particularly 4-fluoro-3-nitrophenyl azide, acyl azides (—CO—$N_3$) such as benzoyl azide and methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of latent reactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha- diazoacetates (—CO—$CHN_2$—CO—O—) such as t-butyl alpha diazoacetoacetate. Other latent reactive groups include the aliphatic azo compounds such as azobisisobutyronitrile, the diazirines (—$CHN_2$) such as 3-trifluoromethyl-3-phenyldiazirine, the ketenes (—CH=C=O) such as ketene and diphenylketene and photoactivatable ketones such as benzophenone and acetophenone. Peroxy compounds are contemplated as another class of latent reactive groups and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate.

Upon activation of the latent reactive groups to cause covalent bond formation to the surfaces to which charged molecules are to be attached, the polymer molecules are covalently attached to the surfaces by means of residues of the latent reactive groups. Exemplary latent reactive groups, and their residues upon activation, are as follows:

| Latent Reactive Group | Residue Functionality |
| --- | --- |
| aryl azides | amine R—NH—R' |
| acyl azides | amide R—CO—NH—R' |
| azidoformates | carbamate R—O—CO—NH—R' |
| sulfonyl azides | sulfonamide R—$SO_2$—NH—R' |
| phosphoryl azides | phosphoramide $(RO)_2PO$—NH—R' |
| diazoalkanes | new C—C bond |
| diazoketones | new C—C bond & ketone |
| diazoacetates | new C—C bond & ester |
| beta-keto-alpha-diazoacetates | new C—C bond & beta-ketoester |
| aliphatic azo | new C—C bond |
| diazirines | new C—C bond |
| ketenes | new C—C bond |
| photoactivated ketones | new C—C bond & alcohol |
| dialkyl peroxides | ethers |
| diacyl peroxides | esters & new C—C bonds |
| peroxyesters | ethers, esters, and new C—C bonds |

The supporting surface of the bioreactor of this invention desirably has a mole ratio of positively-charged molecule to the cell adhesion factor in the range of about $10^3$:1 to about $10^{10}$:1. It is to be understood that the mole ratio will vary, e.g., according to the size of cell adhesion factor used. For example, if the cell adhesion factor is an intact cell adhesion protein the mole ratio of positively-charged groups to the cell adhesion factor is desirably in the range of about $10^4$:1 to about $10^{10}$:1.

The reason that the presence of both a cell adhesion factor and a positively-charged molecule on a bioreactor surface result in better initial cell attraction and better attachment and growth of cells to bioreactor surfaces is not thoroughly understood. While not wishing to be bound by this theory, we think it likely that positively-charged molecules attract and cause initial attachment of cells to the bioreactor surfaces, thus bringing the cells into functional proximity with the cell adhesion factors which then bind the cells more firmly and promote cell spreading.

In cell culture systems used for large-scale production of cells, the culture media must be mixed or perfused to replenish nutrients and to remove waste products from cells. The shear forces that result from the culture medium passing over cell culture surfaces interfere with the attachment of cells. These shear forces are usually greatest in stirred microcarrier bioreactors, less in roller bottles, and least in hollow fiber bioreactors. However, in each of these bioreactor systems, certain commercially important cell lines do not attach well. The present invention can be employed to improve cell attachment and growth in such bioreactor systems.

Since the invention improves cell attachment in the presence of disruptive shear forces, the immobilized cell adhesion factors and positively-charged molecules are preferably tenaciously bound to the culture surface to firmly anchor the attached cells. Covalent immobilization is the preferred method for providing such tenacious immobilization of the cell adhesion factors and positively-charged molecules. Results presented in Example 8 demonstrate that the exemplified cells bind faster and more tenaciously to covalently immobilized cell adhesion proteins and positively-charged molecules than to the same reagents when they are adsorbed.

The invention is further illustrated by the following nonlimiting examples.

EXAMPLE 1

Preparation of Microcarriers and Reagents
Microcarder Beads

Microcarrier beads suspended in spinner flasks and rotated vials were used as bioreactor configurations, since the beads can be readily removed at timed intervals to determine the density of attached cells. Three types of microcarrier beads were used for surface modification: gelatin-coated dextran (Cytodex 3 from Pharmacia Fine Chemicals, Uppsala, Sweden) and polystyrene (100 micrometer diameter polystyrene/divinyl benzene beads from Seradyn, Inc. Indianapolis, Ind.), and collagen-coated polystyrene microcarriers (Solohill Engineering Inc.). Dextran is currently the most widely used microcarrier material but has the disadvantage of being both porous and compressible; both are properties that complicate the harvesting of products secreted into the media. Polystyrene was used as a noncompressible alternate.

Polystyrene beads with an average diameter of 100 micrometers were used. Cell attachment and growth on Cytodex 1 and Cytodex 3 beads (both from Pharmacia) with controlled charge and immobilized gelatin, respectively, were assayed as controls for commercially available surface-modified beads. The Cytodex beads have respective average diameters of 180 and 175 micrometers.

Reagents

Denatured (acid cured) porcine skin gelatin (Type A, 300 bloom from Sigma) was used for immobilization onto polystyrene beads. This gelatin is composed mostly of type I collagen and is very similar to the acid denatured porcine skin type I collagen that is immobilized onto dextran beads to produce Cytodex 3 microcarriers. The remaining cell adhesion proteins used were undenatured and consisted of human placental type IV collagen (from Sigma), and human fibronectin.

Seven reagents were used to increase the positive charge density on microcarrier beads. Polylysine (poly-DL-lysine, MW 15,000 to 30,000 from Sigma) and chitosan (86% deacetylation, 0.8% w/v in 0.5% acetic acid having a viscosity of 1200 centiposes; obtained from Maripol Systems Inc., Excelsior, Minn.) are large polymers with high densities of primary amines. Dimethylaminopropylamine (DMAPA; from Aldrich) was immobilized via the primary amine so that a tertiary amine remained to provide a positive charge at physiologic pH. This tertiary amine is similar to that provided by the N,N-diethylaminoethyl (DEAE) groups on Cytodex 1 beads.

A polymer possessing reactive primary amines was prepared by polymerization of an amine-containing monomer, N-(3-aminopropyl)methacrylamide (APMA). The polymerization was run one hour at room temperature in an aqueous solvent using ammonium persulfate and N,N,N',N'-tetramethylethylenediamine (TMEDA) as catalysts. The polymer was purified by dialysis against deionized water and was isolated by lyophilization.

A polymer possessing quaternary ammonium chloride groups in addition to the reactive primary amines was prepared by a copolymerization of inethacrylamidopropyl trimethylammonium chloride (MAPTAC) with APMA. Two ratios of the monomers were used: 75:25 and 50:50 APMA to MAPTAC. The polymerization was run one hour at room temperature in an aqueous solvent using ammonium persulfate and TMEDA as catalysts. The polymer was purified by dialysis against deionized water and was isolated by lyophilization.

Poly(ethylenimine) (PEI) (average M.W. 50,000 to 60,000) was-purchased from Aldrich Chemical Company.

A heterobifunctional crosslinking agent (BBA-EAC-NOS; 4-benzoylbenzoic acid-epsilonaminocaproic acid -N-oxysuccinimide) was synthesized and used to immobilize cell adhesion proteins and positively-charged molecules onto polystyrene beads. Upon photoactivation, the BBA (4-benzoylbenzoic acid) synthetic polymer forms a highly reactive intermediate that couples to the carbon-hydrogen bonds of carbon-based polymers.

The EAC (epsilon amino caproic acid) provides a 6-carbon spacer between the photogroup and the biomolecule. Finally, the NOS synthetic polymer (N-oxysuccinimide) provides a functional group for crosslinking to primary amines on biomolecules.

BBA-EAC-NOS was synthesized by standard reaction procedures. BBA was converted to the acyl chloride with oxalyl chloride and reacted from toluene with EACA in aqueous NaOH with vigorous stirring. The resulting BBA-EACA was extracted with ethyl acetate and reacted with N-hydroxysuccinimide through activation with dicyclohexylcarbodiimide to produce the active ester. The crude BBA-EAC-NOS was recrystallized from hot ethanol and stored dry.

The starting materials are available commercially. 4-benzoylbensoic acid is available from Aldrich Chemical Company (Milwaukee, Wis.). Other reagents were of the highest available purity and were procured as needed from chemical supply companies.

EXAMPLE 2

Immobilization of Cell Adhesion Factors and Positively-charged Molecules onto Microcarrier Beads

Preparation of Tritiated Cell Adhesion Proteins

Tritiated tracers of each cell adhesion protein were prepared and used to quantitate protein immobilization. The amines of gelatin, type IV collagen, and fibronectin were tritiated by methylation with formaldehyde, followed by reduction with [$^3$H]NaBH$_4$. The tritiated protein derivatives were separated from excess radiolabel by exhaustive dialysis. The specific activities of the radiolabeled proteins were determined by UV spectroscopy/microbiuret protein assay and liquid scintillation spectrometry.

Immobilization of Cell Adhesion Factors and Positively-charged Polymers onto Polystyrene Beads The heterobifunctional crosslinking agent, BBA-EAC-NOS, was used to covalently immobilize each of the cell adhesion proteins (gelatin, type IV collagen, fibronectin) and two of the positively-charged molecules (polylysine and DMAPA) onto polystyrene beads. The BBA-EAC-NOS was added to the polystyrene beads and allowed to adsorb. Next, the proteins and/or positively-charged molecules were added and allowed to react with the NOS synthetic polymer to produce covalent coupling to the spacer. Then the beads were photoactivated (at 320 nm) to covalently immobilize the spacer (and covalently coupled cell adhesion proteins and/or positively-charged molecules) to the polystyrene beads. Finally, loosely adherent proteins and positively-charged molecules were removed by overnight washing with the mild detergent Tween 20 in phosphate buffered saline (pH 7.2).

Immobilization of Positively-charged Polymers on Cytodex 3 Beads

Polylysine, chitosan, and DMAPA were individually immobilized onto Cytodex 3 beads. Chitosan was dialyzed exhaustively against pH 4 deionized water before use. Cytodex 3 beads and each of the amine sources were mixed in 0.25 M MES (2[N-morpholino]ethanesulfonic acid) buffer at pH 5. EDC (1-ethyl-3-[dimethylaminopropyl]carbodiimide)powder was added in several aliquots at 15 minute intervals to the final concentration of 0.1 M. The bead suspensions were agitated during the reaction. Finally, the beads were washed with Tween 20 in PBS to remove loosely adherent molecules.

Immobilization of Positively-charged Polymers onto SoloHill Collagen-coated Microcarriers Collagen-coated polystyrene microcarriers (Model number C102-1521) (150–210 μm diameter) were obtained from SoloHill Engineering Inc. and modified by using glutaraldehyde to covalently couple poly(lysine), poly(APMA), PEI, or poly(APMA/MAPTAC) to the collagen surface. The collagen-coated microcarriers were first activated with glutaraldehyde in deionized water. The microcarriers were then washed with phosphate buffered saline (PBS) followed by deionized water. Then, the positively-charged polymer was added and allowed to couple to the glutaraldehyde-activated collagen. The microcarriers were washed again in deionized water and PBS to remove uncoupled positively-charged polymers. Finally, any unreacted glutaraldehyde was blocked by addition of dimethylaminopropylamine (DMAPA), and the microcarriers were washed to remove residual DMAPA.

EXAMPLE 3

Cell Culture

Cell Types and Culture Conditions

Green monkey kidney (Vero) cells, Chinese hamster ovary (CHO) cells, normal rat kidney fibroblast (NRK-49F) cells, and Madin Darby canine kidney (MDCK) cells were purchased from ATCC. All four cell types were passaged and maintained in 75 cm$^2$ flasks at 37° C. in a 5 % $CO_2$ environment. Vero and NRK-49F cells were cultured in Dulbecco's Modified Eagles's Medium (DMEM), CHO cells were cultured in Ham's F-12 Nutrient Mixture, and MDCK cells were cultured in Minimum Essential Medium (MEM) with Earle's salts. With the Vero and CHO cells, the medium was supplemented with 10% fetal bovine serum (FBS), 2 mM L-glutamine, 20 mM HEPES buffer, 1 mM sodium pyruvate, 100 ug/ml streptomycin, and 100 units/ml penicillin (final pH 7.1). With the NRK-49F cells, the DMEM was supplemented with 5% FBS, 2 mM L-glutamine, 1 mM sodium pyruvate, non-essential amino acids (0.1 mM each), 100 ug/ml streptomycin, 100 units/ml penicillin, and 0.25 ug/ml of amphotericin B (final pH 7.1). With the MDCK cells, the MEM was supplemented with 10% FBS, 2 mM L-glutamine, non-essential amino acids (0.1 mM each), and 100 ug/ml streptomycin, 100 units/ml penicillin, and 0.25 ug/ml of amphotericin B (final pH 7.1).

In order to standardize the physiology of cells prior to each experiment, cells were passed into 150 cm$^2$ flasks 2 to 3 days prior to inoculation of microcarrier beads. Cells were trypsinized (0. 05 % trypsin, 0.53 mM EDTA in PBS) for removal from the flasks. For the microcarrier experiments, the cells were centrifuged to remove the trypsin medium and resuspended to about $1 \times 10^6$ cells/ml in culture medium. The viable cell concentration was determined by Trypan dye exclusion (0.4 % Trypan blue in 0.9% saline).

Initial Screening for Cell Attachment in 20 ml Liquid Scintillation Vials

A small scale assay was used to initially assay cell attachment to each modified microcarrier bead type. By allowing small quantities of beads and cells to be used, this assay allowed more types of bead coatings to be tested than would be possible if all assays were conducted in the larger spinner flask assays.

For the small scale cell attachment assay, 2 mg/ml of Cytodex 1 (beating positively-charged polymers) and Cytodex 3 (bearing collagen) beads or 20 mg/ml of coated polystyrene beads were used. These respective bead concentrations produced the same volumes of beads per ml of media. After swelling and equilibration of each bead type in cell culture media, the respective volumes occupied per mg dry weight of packed Cytodex 1, Cytodex 3, or polystyrene beads were 20 ul, 17 ul, and 1.7 ul. For these cell attachment assays the volumes of packed beads used per ml of media were 34 ul beads/ml for Cytodex 3 and polystyrene beads and 40 ul beads/ml for Cytodex 1 beads.

The assays were conducted in siliconized 20 ml glass liquid scintillation vials. The beads (34 or 40 ul/ml) and cells ($1.5 \times 10^5$ cells/ml) were added to a total volume of 15 ml per vial. Then the beads were kept in suspension by continuously rotating the vials with a motion that prevented the beads from settling and rubbing against each other. To achieve this motion, the vials were attached at a 45 degree angle to a Labquake vial rotator (Lab Industries Model No. 400-110) and rotated at 8 rpm. At timed intervals, the vials were removed, the beads were allowed to settle for about 30 seconds, and aliquots of the cells remaining in suspension were removed and counted. For the cell counts, the cells were stained by mixing with an equal volume of crystal violet (0.1% w/w) in 0.1 M citric acid, and then counted with a hemocytometer. Cell depletion from the medium was used as an indicator of cells attached to beads.

To verify that cells removed from the medium were indeed attached to microcarriers (and not lysed), cells attached to microcarriers were quantitated at the end of each cell attachment assay. One ml aliquots of well-agitated carrier medium were removed, the microcarders were allowed to settle, and the settled microcarriers were resuspended in crystal violet/citric acid as described above. After incubating 1 hour at 37° C., the suspension was sheared by sucking into and out of a Pasteur pipet to release nuclei, which were quantitated with a hemocytometer.

Cell Culture and Assays in Spinner Flasks

Microcarriers were cultured using previously described protocols with 100 ml cultures being maintained in 250 ml spinner vessels and stirred with suspended magnetic impellers (50 rpm). The concentrations of beads and cells were the same as for the scintillation vial cell attachment assays. The bead concentrations were 2 mg/ml for Cytodex 1 and 3 and 20 mg/ml for polystyrene beads and the cell concentration was $1.5 \times 10^5$ cells/ml for each cell type. The kinetics of cell attachment were assayed as a decrease in supernatant cell concentration using a protocol similar to that used for the scintillation vial cell attachment assays. For sample removal the agitation was stopped briefly (about 30 seconds) at which time the microcarriers settled and a supernatant sample was removed for cell quantitation as described above.

Starting at 4 hours, cells attached to microcarders were assayed using the protocol described for quantitating cells attached to microcarriers at the end of the scintillation vial assays. All cultures were continued and assayed at daily intervals through 5 days; and at 2 to 3 day intervals thereafter. At 2 to 3 day intervals, the beads were allowed to settle and 50–75% of the culture medium was replaced with fresh medium.

The morphology of the cells growing on microcarders was also assayed at timed intervals. Briefly, 0.1 ml aliquots of well-agitated carrier medium was removed and placed into individual wells of a 24-well cell culture plate. Then one drop (25 ul) of 0.5 % crystal violet in 40% ethanol was added and incubated 30 seconds to fix and stain the cells. Then 3.0 ml of PBS was added to each well, and the cells were observed by bright field microscopy at 200X magnification.

EXAMPLE 4

Quantitation of Tritiated Proteins Immobilized onto Polystyrene Beads

The heterobifunctional crosslinking agent (BBA-EAC-NOS) was used to covalently immobilize cell adhesion proteins onto polystyrene beads using the protocol described above (Example 2). An initial experiment was conducted with [$^3$H]gelatin to determine: 1) the efficiency of protein binding and the maximum protein loading that could be achieved using the covalent immobilization protocol; and 2) how covalent loading compares to adsorption in the absence of BBA-EAC-NOS. Results shown in Table I show that loading of covalently bound gelatin saturated at about 3.5 ug per 10 ul of beads. The efficiency of gelatin loading was 93% when added at 3 ug gelatin per 10 ul beads; whereas at the higher levels of added gelatin, the percentage of binding decreased with little increase in total loading. These results indicate that 3 ug gelatin added per 10 ul beads would couple quite efficiently and yield nearly maximal loading. This ratio of gelatin added to beads was used for the remainder of the study.

TABLE I

CELL ADHESION PROTEINS IMMOBILIZED ONTO POLYSTYRENE BEADS.

| Protein | Covalent or Adsorbed | Protein added /10 ul beads (ug) | Protein Bound /10 ul beads (ug) | % Immob. | Fold Increase (C/A) |
|---|---|---|---|---|---|
| Gelatin | C | 3.0 | 2.8 | 93 | 4.8 |
| Gelatin | A | 3.0 | 0.58 | 19 | — |
| Gelatin | C | 7.3 | 3.3 | 45 | 4.6 |
| Gelatin | A | 7.3 | 0.70 | 9.6 | — |
| Gelatin | C | 18.0 | 3.4 | 19 | 4.3 |
| Gelatin | A | 18.0 | 0.80 | 4.4 | — |
| IV Collagen | C | 0.96 | 1.11 | 116 | 7.9 |
| IV Collagen | A | 0.96 | 0.14 | 14 | — |
| Fibronectin | C | 1.22 | 1.08 | 89 | 3.2 |

TABLE I-continued

CELL ADHESION PROTEINS IMMOBILIZED ONTO POLYSTYRENE BEADS.

| Protein | Covalent or Adsorbed | Protein added /10 ul beads (ug) | Protein Bound /10 ul beads (ug) | % Immob. | Fold Increase (C/A) |
|---|---|---|---|---|---|
| Fibronectin | A | 1.22 | 0.34 | 28 | — |

When covalent immobilization of gelatin is compared to adsorption (at 3–18 ug added per 10 ul beads), it is seen that 4-to 5-fold more protein is immobilized via the BBA-EAC-NOS than is immobilized by adsorption. Results presented below (Example 8) demonstrate that cells bind faster and more tenaciously to covalently immobilized cell adhesion proteins and positively-charged polymers than do the same reagents when they are adsorbed without covalent bonding.

Tritiated type IV collagen and fibronectin exhibited similar binding characteristics to those observed with gelatin (Table I). Each of these proteins was added at a concentration of about 1 ug per 10 ul beads and covalently coupled with an efficiency of 89% or higher. Also, each protein produced several fold more protein covalently immobilized than adsorbed. For the remaining experiments, 3 ug of gelatin or 1 ug type IV collagen or fibronectin were added per 10 ul polystyrene beads.

These results clearly demonstrate that this covalent coupling technology utilizing BBA-EAC-NOS produces both efficient binding of proteins to polystyrene beads, and significantly increases the protein loading density when compared to adsorption.

EXAMPLE 5

Calculation of Cell Attachment Rate Constants

Cytodex 1 microcarriers have a high density of positive charges and are typically reported to produce faster cell attachment than do Cytodex 3 microcarders. In Table II, the initial rate of cell attachment to each microcarrier type is expressed as a rate constant, which was calculated from the formula:

$$K(\text{min}^1) = \frac{\ln[\text{initial cell no.}] - \ln[\text{final cell no.}]}{\text{min.}}$$

as previously described (Himes, V. B. and W. S. Hu, 1987, Biotech. Bioeng. 29:1155–1193). Table II shows that: 1) Vero cells attach about twice as fast to Cytodex 1 microcarders as to Cytodex 3 microcarders, and 2) both cell attachment assays produced nearly identical results.

As was described in Example 2, the cells attached at each assay time were determined by quantitating the removal of cells from the culture medium. However, to verify that the removed cells had bound to microcarriers (and had not lysed), the cells attached to microcarriers were also quantitated at the end of each assay (at 60 minutes). Table II shows that 92–100% of the cells were attached to the beads at 60 minutes, therefore verifying that cell depletion from the medium was due to attachment to the microcarriers.

TABLE II

RATE CONSTANTS FOR ATTACHMENT OF VERO CELLS TO CYTODEX 1 AND CYTODEX 3 MICROCARRIERS ASSAYED IN EITHER THE SCINTILLATION VIAL ASSAY OR THE SPINNER FLASK ASSAY.

| Assay Protocol | Microcarrier Type | Rate Constant (min$^{-1}$) | % of Cells Attached at 60 min |
|---|---|---|---|
| Vial | Cytodex 1 | 0.212 | 97 |
| Vial | Cytodex 3 | 0.115 | 92 |
| Flask | Cytodex 1 | 0.226 | 100 |
| Flask | Cytodex 3 | 0.129 | 99 |

EXAMPLE 6

Cell Attachment to Cytodex 3 Microcarriers with Added Positively-charged Groups

To determine whether increasing the density of positive charges would increase the rate of cell attachment to Cytodex 3 microcarriers (having collagen on surface), three different molecules were added (using protocols described in Example 2) to introduce positively-charged groups. Chitosan and polylysine each added primary amines, whereas the DMAPA added tertiary amines similar to the DEAE present on Cytodex 1.

Table III shows that each of the molecules used to add positive charges to Cytodex 3 microcarriers increased the cell attachment rates of both Vero and CHO cells. Chitosan was the most effective.

TABLE III

RATE CONSTANTS FOR ATTACHMENT OF CELLS TO CYTODEX 3 MICROCARRIERS MODIFIED BY THE ADDITION OF POSITIVELY-CHARGED GROUPS.

| Microcarrier Type | Cell Type | Rate Constant (min$^{-1}$) | % of Cells Attached at 60 min. |
|---|---|---|---|
| Cytodex 3 | Vero | 0.164 | 96 |
| Cytodex 3 + chitosan | Vero | 0.271 | 93 |
| Cytodex 3 + polylysine | Vero | 0.237 | 94 |
| Cytodex 3 + DMAPA | Vero | 0.204 | 96 |
| Cytodex 3 | CHO | 0.037 | 80 |
| Cytodex 3 + chitosan | CHO | 0.085 | 82 |
| Cytodex 3 + polylysine | CHO | 0.052 | 82 |

EXAMPLE 7

Cell Attachment to Polystyrene Beads with Individually Added Cell Adhesion Proteins or Positively-charged Polymers The positively-charged molecules shown above (Table III) to improve cell attachment to Cytodex 3 microcarriers were individually immobilized onto polystyrene beads (using protocols described in Example 2) and assayed for cell attachment using Vero cells. For each set of cell attachment experiments Cytodex 3 microcarriers were included as a control to verify that the batch of cells exhibited normal attachment kinetics. Results shown in Table IV reveal: 1) no cells attached to uncoated polystyrene (polystyrene-uncoated); and 2) the polylysine coating produced cell attachment comparable to that observed with Cytodex 3 microcarders.

TABLE IV

RATE CONSTANTS FOR ATTACHMENT OF CELLS TO POLYSTYRENE MICROCARRIERS WITH INDIVIDUALLY ADDED POSITIVELY-CHARGED REAGENTS.

| Microcarrier Type | Cell Type | Rate Constant (min$^{-1}$) | % of Cells Attached at 60 min. |
|---|---|---|---|
| Cytodex 3 | Vero | 0.163 | 97 |
| Polystyrene-uncoated | Vero | 0.000 | 0 |
| Polystyrene + polylysine | Vero | 0.169 | 90 |

Cell adhesion proteins were individually immobilized onto polystyrene microcarders (using protocols described in Example 2) and assayed for cell attachment using either Vero or CHO cells. Table V shows that none of the cell adhesion proteins immobilized onto polystyrene beads produced cell attachment equivalent to Cytodex 3 microcarders. With the coated polystyrene microcarders, cell attachment was fastest with type IV collagen, next fastest with gelatin, and slowest with fibronectin.

TABLE V

RATE CONSTANTS FOR ATTACHMENT OF CELLS TO POLYSTYRENE MICROCARRIERS WITH INDIVIDUALLY ADDED CELL ADHESION PROTEINS.

| Experiment Number | Microcarrier Type | Cell Type | Rate Constant (min$^{-1}$) | % of Cells Attached at 60 min. |
|---|---|---|---|---|
| 1 | Cytodex 3 | CHO | 0.043 | 76 |
| 1 | Polystyrene + IV collagen | CHO | 0.034 | 0[a] |
| 1 | Polystyrene + fibronectin | CHO | 0.016 | 27 |
| 2 | Cytodex 3 | Vero | 0.171 | 94 |
| 2 | Polystyrene + IV collagen | Vero | 0.075 | 63 |
| 2 | Polystyrene-uncoated | Vero | 0.0000 | 0 |
| 3 | Cytodex 3 | Vero | 0.115 | 92 |
| 3 | Polystyrene + gelatin | Vero | 0.190 | 97 |
| 4 | Cytodex 3 | Vero | 0.190 | 97 |
| 4 | Polystyrene + fibronectin | Vero | 0.012 | 21 |

[a]The beads coated with type IV collagen showed maximum binding at 20 minutes (49%), after which steadily decreasing percentages of attached cells were measured until no attached cells were observed at 60 minutes.

EXAMPLE 8

Cell Attachment to Polystyrene Beads Coated with Polylysine Plus Either Type IV Collagen or Gelatin When polylysine was added to polystyrene microcarders, it produced cell attachment comparable to Cytodex 3 (Table IV); and of the three cell adhesion proteins tested, type IV collagen and gelatin produced the fastest cell attachment (Table V).

Polystyrene microcarriers were prepared that had immobilized either: 1) polylysine plus type IV collagen, or 2) polylysine plus gelatin. Each reagent combination was immobilized by addition to BBA-EAC-NOS treated polystyrene beads as described in Example 2. Since the polylysine and each protein compete for binding to NOS polymers, the immobilized polylysine decreases the loading level of each protein. The ratios of each protein and polylysine were adjusted so that each protein was immobilized at about 70% of the levels present on the microcarriers used in Table V.

Table VI shows that a combination of polylysine plus either type IV collagen or gelatin added to polystyrene microcarriers produced attachment of each cell type that was equal to or better than attachment to Cytodex 3 microcarriers. Adsorption controls for which the same concentrations of gelatin and polylysine were added in the absence of the crosslinking agent, BBA-EAC-NOS, produced: 1) 50% to 70% decreases in the initial cell attachment rates for each cell type; and 2) an apparent release of Vero cells after initial attachment. This demonstrates the essential contribution of the covalent crosslinking agent.

TABLE VI

RATE CONSTANTS FOR ATTACHMENT OF CELLS TO POLYSTYRENE MICROCARRIERS COATED WITH POLYLYSINE PLUS EITHER TYPE IV COLLAGEN OR GELATIN.

| Experiment Number | Microcarrier Type | Cell Type | Rate Constant ($min^{-1}$) | % of Cells Attached at 60 min. |
|---|---|---|---|---|
| 1 | Cytodex 3 | Vero | 0.162 | 78 |
| 1 | PS + PL + IV collagen | Vero | 0.236 | 92 |
| 1 | PS + PL + gelatin | Vero | 0.193 | 98 |
| 1 | PS + PL + gelatin (ads.) | Vero | 0.104 | 42[a] |
| 2 | Cytodex 3 | CHO | 0.040 | 71 |
| 2 | PS + PL + gelatin | CHO | 0.043 | 82 |
| 2 | PS + PL + gelatin (ads.) | CHO | 0.012 | 27 |

[a]The beads coated with adsorbed reagents showed maximum binding (81%) at 15 minutes, followed by steadily decreasing percentages of cells attached through 60 minutes.
PS = polystyrene
PL = polylysine
ads. = reagents adsorbed to polystyrene beads in the absence of BBA-EAC-NOS

EXAMPLE 9

Spinner Flask Assays

Results from the scintillation vial cell attachment assays indicate that: 1) charged groups added to cytodex 3 microcarriers greatly improved the rate of cell attachment (Table III); and 2) polystyrene beads modified by covalent immobilization of polylysine plus either gelatin or type IV collagen produced cell attachment equal to or better than Cytodex 3 microcarriers (Table VI).

Cell Attachment

Cell attachment was assayed in spinner flasks using the protocol described in Example 3. Table VII, Experiment 1 compares Vero cell attachment with four microcarrier types: Cytodex 1, Cytodex 3, Cytodex 3+chitosan, and polystyrene (PS)+ polylysine (PL)+gelatin. The two microcarrier types coated with both gelatin and a positively-charged polymer produced the fastest rates of initial cell attachment, and all four microcarrier types produced 95–100% cell attachment by 60 minutes.

TABLE VII

RATE CONSTANTS FOR ATTACHMENT OF CELLS TO MICROCARRIERS ASSAYED IN SPINNER FLASKS.

| Experiment Number | Microcarrier Type | Cell Type | Rate Constant ($min^{-1}$) | % of Cells Attached at 60 min. |
|---|---|---|---|---|
| 1 | Cytodex 1 | Vero | 0.226 | 100 |
| 1 | Cytodex 3 | Vero | 0.129 | 99 |
| 1 | Cytodex 3 + chitosan | Vero | 0.290 | 100 |
| 1 | PS + PL + gelatin | Vero | 0.260 | 95 |
| 2 | Cytodex 1 | CHO | 0.112 | 99 |
| 2 | Cytodex 3 | CHO | 0.075 | 96 |
| 2 | Cytodex 3 + chitosan | CHO | 0.134 | 98 |

PS = polystyrene
PL = polylysine

Table VII, Experiment 2 compares CHO cell attachment to several microcarrier types. Cytodex 1 and Cytodex 3+chitosan showed higher rates of cell attachment than did Cytodex 3.

These results agree with the scintillation vial results by confirming that chitosan greatly improves the attachment of both cell types to Cytodex 3 microcarriers.

Cell Growth

Cells attached to microcarriers were assayed initially at 4 hours and later at daily intervals, as described in Example 3. Cell numbers per ml of culture medium are given for days 2 and 8 in Table VIII.

TABLE VIII

CELL GROWTH ON MICROCARRIERS ASSAYED IN SPINNER FLASKS.

| Microcarrier Type | Cell Type | Cells per ml ($\times 10^6$) | |
|---|---|---|---|
| | | Day 2 | Day 8 |
| Cytodex 1 | Vero | 1.3 | 4.4 |
| Cytodex 3 | Vero | 1.6 | 4.2 |
| Cytodex 3 + chitosan | Vero | 2.2 | 7.7 |
| PS + PL + gelatin | Vero | 2.0 | 6.4 |
| Cytodex 1 | CHO | 1.3 | 2.8 |
| Cytodex 3 | CHO | 1.6 | 3.2 |
| Cytodex 3 + chitosan | CHO | 1.8 | 3.3 |

The Vero cells grew best on the two microcarrier types coated with gelatin plus positively-charged groups: polystyrene microcarriers coated with polylysine plus gelatin (PS+ PL+ gelatin) and Cytodex 3 microcarriers coated with chitosan. The CHO cells grew best on Cytodex 3 and Cytodex 3 plus chitosan.

These results clearly show that adding positively-charged groups to gelatin does not decrease cell growth, since the Cytodex 3 plus chitosan produced excellent growth of both cell types and polystyrene coated with gelatin plus polylysine produced excellent Vero cell growth.

EXAMPLE 10

Cell Attachment and Growth on Collagen-coated SoloHill Microcarriers with Added Positively-charged Polymers The positively-charged polymers were covalently coupled to commercial collagen-coated SoloHill microcarders as described in Example 2.

Cell Attachment Assays

The cell attachment protocol described in Example 3 (20 ml vials) was used to measure rates of attachment of both Vero and NRK-49F cells to each microcarder type. Results in Tables IX and X show that the addition of several positively-charged polymers to collagen-coated microcarders dramatically increase the rate of attachment of both Vero and NRK-49F cells. The most reproducable enhancement in cell attachment was produced by APMA and PEI.

TABLE IX

RATE CONSTANTS FOR ATTACHMENT OF VERO CELLS TO SOLOHILL MICROCARRIERS ASSAYED IN 20 ML VIALS.

| Experiment Number | Microcarrier Type | Rate Constant ($min^{-1}$) | % of Cells Attached at 30 min. |
|---|---|---|---|
| 1 | Collagen | 0.00 | 34 |
| 1 | Collagen + APMA | 0.267 | 69 |
| 1 | Collagen + A/M 75:25[a] | 0.097 | 34 |
| 1 | Collagen + polylysine | 0.029 | 9 |
| 2 | Collagen | 0.00 | 0 |
| 2 | Collagen + A/M 50:50[b] | 0.322 | 94 |
| 2 | Collagen + polylysine | 0.444 | 98 |
| 3 | Collagen | 0.051 | 0 |
| 3 | Collagen + APMA | 0.298 | 85 |
| 3 | Collagen + A/M 50:50 | 0.322 | 90 |
| 3 | Collagen + polylysine | 0.205 | 64 |
| 4 | Collagen | 0.000 | 0 |
| 4 | Collagen + PEI | 0.171 | 91 |
| 4 | Collagen + A/M 75:25 | 0.144 | 82 |
| 4 | Collagen + polylysine | 0.048 | 60 |

[a]A/M 75:25 = copolymer of APMA and MAPTAC, with a 75:25 ratio.
[b]A/M 50:50 = copolymer of APMA and MAPTAC, with a 50:50 ratio.

TABLE X

RATE CONSTANTS FOR ATTACHMENT OF NRK-49F CELLS TO SOLOHILL MICROCARRIERS ASSAYED IN 20 ML VIALS.

| Experiment Number | Microcarrier Type | Rate Constant ($min^{-1}$) | % of Cells Attached at 60 min.[a] |
|---|---|---|---|
| 1 | Collagen | 0.013 | 24 |
| 1 | Collagen + APMA | 0.239 | 100 |
| 2 | Collagen | 0.00 | 17 |
| 2 | Collagen + APMA | 0.354 | 97 |
| 2 | Collagen + PEI | 0.310 | 96 |
| 2 | Collagen + A/M 50:50[b] | 0.136 | 68 |
| 2 | Collagen + polylysine | 0.150 | 67 |
| 3 | Collagen | 0.027 | 0 |
| 3 | Collagen + APMA | 0.172 | 92 |
| 3 | Collagen + PEI | 0.204 | 100 |
| 3 | Collagen + A/M 75:25[c] | 0.172 | 97 |
| 3 | Collagen + A/M 50:50[b] | 0.144 | 92 |
| 3 | Collagen + polylysine | 0.151 | 84 |
| 4 | Collagen | 0.000 | 0 |
| 4 | Collagen + APMA | 0.144 | 90 |

[a]In experiment 2, the % of cells attached was assayed at 30 min.
[b]A/M 50:50 = copolymer of APMA and MAPTAC, with a 50:50 ratio.
[c]A/M 75:25 = copolymer of APMA and MAPTAC, with a 75:25 ratio.

Growth of Vero and NRK-49F cells on each type of microcarrier that was utilized in Tables IX and X was monitored in a non-agitated assay. For this assay, 300 mg of each type of microcarder was placed in individual wells of six-well tissue culture plates. Then, 3 ml of cells (at $5 \times 10^5$/ml) were added to each well and cultured for 4 days (NRK-49F cells) or 9 days (Vero cells). With the NRK-49F cells, there was no significant difference in cell numbers at 4 days on collagen-coated microcarriers with or without added APMA, PEI or polylysine. Whereas, at 8 days, about twice as many Vero cells were growing on collagen-coated microcarriers modified with APMA, PEI, and polylysine as with unmodified collagen-coated microcarriers. These growth assays in non-agitated medium demonstrate that the modified microcarriers support cell growth that is at least equal to that of non-modified collagen-coated microcarriers.

In stirred reactors, superior cell growth was observed on collagen-coated microcarriers with added poly(APMA) as compared to unmodified collagen-coated microcarrriers (Table XI). The cell growth assay was conducted as described in Example 9, with the exceptions that: 1) a different type of-spinner flask was used (Wheaton flasks), 2) the stirring speed was 24 rpm, and 3) the reactors were inoculated with a lower cell number ($5.8 \times 10^4$ cells/ml). Also, for the first 24 hours, ½ volume (50 ml) was used and the stirring rate was 20 rpm. At time intervals, aliquots of microcarriers were removed and evaluated for attached cells as described for Example 9. Table XI shows faster initial cell growth on the collagen+APMA microcarriers, with greater cell numbers being present on these microcarriers through day 10. The faster initial cell growth is presumably due, at least in part, to the greater efficiency of initial cell attachment.

TABLE XI

GROWTH OF MDCK CELLS ON SOLOHILL MICROCARRIERS ASSAYED IN SPINNER FLASKS.

| Microcarrier Type | Cells per ml ($\times 10^5$) | | | |
|---|---|---|---|---|
| | Day 1 | Day 3 | Day 6 | Day 10 |
| Collagen | 7.0 | 10 | 24 | 43 |
| Collagen + APMA | 9.5 | 23 | 49 | 57 |

While a preferred embodiment of the present invention has been described in these Examples, it should be understood that various changes, adaptations and modifications may be made therein without departing from the spirit of the invention and the scope of the appended claims.

What is claimed is:

1. A cell culture support comprising a support material in the form of a microcarrier and comprising a supporting surface for the attachment of cells, the surface bearing a combination comprising:

a positively-charged molecule selected from a group consisting of polylysine, chitosan, poly(ethyleneimine), and acrylics polymerized from acrylamide or methacrylamide and incorporating positively-charged groups in the form of primary, secondary, or tertiary amines, or quaternary salts, and a cell adhesion factor selected from the group consisting of fibronectin, laminin, collagen, vitronectin and tenascin, and active fragments and synthetic analogs having a cell binding domain thereof, wherein either (a) the positively-charged molecule and the cell adhesion factor are covalently bound to the supporting surface, or (b) the positively-charged molecule and the cell adhesion factor are covalently bound to one another and either the positively-charged molecule or the cell adhesion factor is covalently bound to the supporting surface, or (c) either the positively-charged molecule or the cell adhesion factor, or both, are provided in the form of a stable coating noncovalently bound around the surface of the supporting material.

2. A support according to claim 1 wherein the surface bears the combination of (a).

3. A support according to claim 1 wherein the surface bears the combination of (b).

4. A support according to claim 1 wherein the surface bears the combination of (c).

5. A support according to claim 1 wherein the support material is selected from the group consisting of polystyrene and polypropylene.

6. A support according to claim 1 wherein the support material is polystyrene.

7. A method of preparing a cell culture support comprising the steps of:

providing a support material in the form of a microcarrier and comprising a support surface for the attachment of cells and applying to the support surface a combination comprising:

a positively-charged molecule selected from a group consisting of polylysine, chitosan, poly(ethyleneimine), and, acrylics polymerized from acrylamide or methacrylamide and incorporating positively-charged groups in the form of primary, secondary, or tertiary amines, or quaternary salts, and a cell adhesion factor selected from the group consisting of fibronectin, laminin, collagen, vitronectin and tenascin, and active fragments and synthetic analogs having a cell binding domain thereof, wherein either (a) the positively-charged molecule and the cell adhesion factor are covalenfly bound to the supporting surface, or (b) the positively-charged molecule and the cell adhesion factor are covalently bound to one another and either the positively-charged molecule or the cell adhesion factor is covalently bound to the supporting surface, or (c) either the positively-charged molecule or the cell adhesion factor, or both, are provided in the form of a stable coating noncovalently bound around the surface of the supporting material.

8. A method according to claim 7 wherein the surface bears the combination of (a).

9. A support according to claim 7 wherein the surface bears the combination of (b).

10. A support according to claim 7 wherein the surface bears the combination of (c).

11. A support according to claim 7 wherein the support material is selected from the group consisting of polystyrene and polypropylene.

12. A support according to claim 7 wherein the support material is polystyrene.

* * * * *

UNITED STATES PATENT AND TRADEMARK OFFICE
CERTIFICATE OF CORRECTION

PATENT NO. : 5,512,474
DATED : April 30, 1996
INVENTOR(S) : David L. Clapper and Wei-Shou Hu It is certified that error appears in the above-indentified patent and that said Letters Patent is hereby corrected as shown below:

Column 1, line 48, replace "Micro-carders" with --Micro-carriers--.

Column 2, line 38, replace "microcarders" with --microcarriers--.

Column 2, line 51, replace "meg/g" with --meq/g --.

Column 2, line 61, replace "Microcarder" with --Microcarrier--.

Column 2, line 66, replace "microcarders" with --microcarriers--.

Column 3, line 1, replace "Microcarders" with --Microcarriers--.

Column 3, line 22, replace "Microcarder" with --Microcarrier--.

Column 3, line 30, replace "Microcarder" with --Microcarrier--.

Column 3, line 34, replace "microcarders" with --microcarriers--.

Column 3, line 54, replace "beating" with --bearing--.

Column 5, line 45, replace "tetrafiuoroethylene" with --tetrafluoroethylene--.

Column 7, line 15, replace "carded" with --carried--.

Column 8, line 23, replace "carded" with --carried--.

UNITED STATES PATENT AND TRADEMARK OFFICE
CERTIFICATE OF CORRECTION

PATENT NO. : 5,512,474
DATED : April 30, 1996
INVENTOR(S) : David L. Clapper and Wei-Shou Hu It is certified that error appears in the above-indentified patent and that said Letters Patent is hereby corrected as shown below:

Column 8, line 40, replace "microcarder" with --microcarrier--.

Column 11, line 4, replace "Microcarder" with --Microcarrier--.

Column 11, line 62, replace "inethacrylamidopropyl" with --methacrylamidopropyl--.

Column 12, line 29, replace "zoylbensoic" with --zoylbenzoic--.

Column 14, line 21, replace "beating" with --bearing--.

Column 14, line 52, replace "microcarders" with --microcarriers--.

Column 15, line 9, replace "microcarders" with --microcarriers--.

Column 15, line 17, replace "microcarders" with --microcarriers--.

Column 16, line 45, replace "microcarders" with --microcarriers--.

Column 16, line 57, replace "microcarders" with --microcarriers--.

UNITED STATES PATENT AND TRADEMARK OFFICE
CERTIFICATE OF CORRECTION

PATENT NO. : 5,512,474
DATED : April 30, 1996
INVENTOR(S) : David L. Clapper and Wei-Shou Hu It is certified that error appears in the above-indentified patent and that said Letters Patent is hereby corrected as shown below:

Column 17, line 57, replace "microcarders" with --microcarriers--.

Column 17, line 67, replace "carders" with --carriers--.

Column 18, line 15, replace "microcarders" with --microcarriers--.

Column 18, line 19, replace "microcarders" with --microcarriers--.

Column 18, line 20, replace "microcarders" with --microcarriers--.

Column 18, line 54, replace "microcarders" with --microcarriers--.

UNITED STATES PATENT AND TRADEMARK OFFICE
CERTIFICATE OF CORRECTION

PATENT NO. : 5,512,474
DATED : April 30, 1996
INVENTOR(S) : David L. Clapper and Wei-Shou Hu It is certified that error appears in the above-indentified patent and that said Letters Patent is hereby corrected as shown below:

Column 20, line 66, replace "microcarders" with --microcarriers--.

Column 21, line 5, replace "microcarder" with --microcarrier--.

Column 21, line 7, replace "microcarders" with --microcarriers--.

Column 21, line 62, replace "microcarder" with --microcarrier--.

Column 23, line 18, replace "and," with --and--.

Column 24, line 2, replace "covalenfly" with --covalently--.

Signed and Sealed this

Twentieth Day of August, 1996

Attest:

BRUCE LEHMAN

Attesting Officer          Commissioner of Patents and Trademarks